(12) United States Patent
Watanabe et al.

(10) Patent No.: US 8,163,564 B2
(45) Date of Patent: Apr. 24, 2012

(54) COMPUTER CONNECTED TO A SMEAR PREPARING APPARATUS

(75) Inventors: Toshio Watanabe, Oonojyo (JP); Mieko Asada, Akashi (JP)

(73) Assignee: Sysmex Corporation, Kobe (JP)

( * ) Notice: Subject to any disclaimer, the term of this patent is extended or adjusted under 35 U.S.C. 154(b) by 1062 days.

(21) Appl. No.: 11/223,475

(22) Filed: Sep. 8, 2005

(65) Prior Publication Data

US 2006/0051240 A1 Mar. 9, 2006

(30) Foreign Application Priority Data

Sep. 8, 2004 (JP) ................................ 2004-0260432

(51) Int. Cl.
*G01N 1/00* (2006.01)
(52) U.S. Cl. ............. 436/174; 422/63; 422/65; 422/66; 422/67
(58) Field of Classification Search .................... 422/63, 422/99, 100; 436/174
See application file for complete search history.

(56) References Cited

U.S. PATENT DOCUMENTS

| 5,209,903 A | 5/1993 | Kanamori et al. |
| 5,650,332 A * | 7/1997 | Gao et al. ....................... 436/174 |
| 2003/0003022 A1 * | 1/2003 | Tamura et al. .................. 422/99 |
| 2003/0138355 A1 * | 7/2003 | Tamura et al. .................. 422/63 |
| 2005/0025672 A1 | 2/2005 | Nakaya et al. |

* cited by examiner

*Primary Examiner* — In Suk Bullock
*Assistant Examiner* — Robert Eom
(74) *Attorney, Agent, or Firm* — Brinks Hofer Gilson & Lione

(57) ABSTRACT

A computer for receiving first and second sample attribute information regarding attributes of a sample, for determining parameter identification information for identifying a smear control parameter on the basis of the first sample attribute information, for generating first and second instruction to make a smear preparing apparatus prepare a smear of a sample, the first instruction including the parameter identification information, and the second instruction including the second sample attribute information, for transmitting the first and second instruction to the smear preparing apparatus is disclosed.

13 Claims, 8 Drawing Sheets

| HCT | Smear-ing Level | Smear Control Parameter | | | |
|---|---|---|---|---|---|
| | | Speed (mm/sec) | Angle (degree) | Fitting time (sec) | Amount of dispensed sample (μL) |
| Less than 20 | 1 | 135 | 20 | 3.0 | 4 |
| 20~30 | 2 | 120 | 17 | 2.0 | 4 |
| 30~40 | 3 | 105 | 17 | 2.0 | 3 |
| 40~50 | 4 | 90 | 15 | 2.0 | 3 |
| Over 50 | 5 | 75 | 13 | 2.0 | 2 |
| | 6 | 120 | 15 | 2.0 | 3 |
| | 7 | 90 | 17 | 3.0 | 4 |
| | 8 | 105 | 17 | 2.0 | 4 |
| | 9 | 110 | 15 | 2.0 | 3 |
| | 10 | 90 | 20 | 3.0 | 3 |

| Smearing level | Smearing Level Conditions | | | |
|---|---|---|---|---|
| | WBC | RBC | Abnormality message | Medical record information |
| 6 | 40<WBC<70 | 300<RBC<500 | None | None |
| 7 | 40<WBC<70 | 300<RBC<500 | None | Pediatrics |
| 8 | 70<WBC<120 | 10<RBC<20 | Lymphopenia | Leukemia |
| 9 | 70<WBC<120 | 10<RBC<20 | Lymphocytosis | Leukemia |
| 10 | 40<WBC<70 | 500<RBC<700 | Neutropenia | Leukemia |

COMPUTER CONNECTED TO A SMEAR PREPARING APPARATUS

This application claims priority under 35 U.S.C. §119 to Japanese Patent Application No. 2004-260432 filed Sep. 8, 2004, the entire content of which is hereby incorporated by reference.

FIELD OF THE INVENTION

The present invention relates to a computer connected to a smear preparing apparatus for preparing a smear of sampled blood, bone-marrow fluid and the like.

BACKGROUND

Conventionally, in order to observe blood or the like by a microscope or the like, a smear preparing apparatus in which blood or the like is dropped on a slide glass and smeared by a spreader glass (smearing member) to generate a smear is used.

Since each sample has different characteristics such as particle density, viscosity and the like, if the smear is always generated under the same condition, the smear becomes unsuitable for observation in some samples.

Therefore, there is known a smear preparing apparatus in which the smearing parameter is set every sample based on a measurement result from a blood analyzer (refer to U.S. Pat. No. 5,209,903).

According to such conventional apparatus, the smearing parameter is determined based on a hematocrit value, for example. In addition, since it is known that blood viscosity is increased as a hemoglobin amount is increased in general, it is considered that the smearing parameter is set based on the measurement result of the hemoglobin amount.

In addition, although the method of setting the smearing parameter by the above conventional apparatus is very effective when the smear is automatically generated, it does not respond to a case of the special sample or various kinds of user's needs.

For example, although the hematocrit value of a leukemia patient is normal or slightly small, it has been found that the WBC (White Blood Cell) of the leukemia patient is weak and liable to be destroyed.

When a blood smear of such patient is made, it is necessary to make it thicker than the smear made under the smearing parameter based on the normal hematocrit value when the blood on the slide glass is smeared by the spreader glass, so as not to destroy the WBC.

In addition, observers who observe the smear by a microscope have different demands for the smear. That is, some observers want to observe thin and spread smear and some observers want to observe the smear thickly collected in a small region.

BRIEF SUMMARY

The scope of the present invention is defined solely by the appended claims, and is not affected to any degree by the statements within this summary.

The present invention provides a computer used for preparing a smear of a sample, which is easy to observe.

A first aspect of the present invention is a computer connected to a smear preparing apparatus for preparing a smear of a sample on a slide glass based on a smear control parameter, the computer comprising: a receiver for receiving first and second sample attribute information regarding attributes of a sample; an identification information determining means for determining parameter identification information for identifying the smear control parameter on the basis of the first sample attribute information; an instruction generating means for generating first and second instruction to make the smear preparing apparatus prepare the smear of a sample, the first instruction including the parameter identification information determined by the identification information determining means, and the second instruction including the second sample attribute information; and a transmitter for transmitting the first and second instruction generated by the instruction generating means to the smear preparing apparatus, wherein when the parameter identification information is determined by the identification information determining means, the instruction generating means generates the first instruction and the transmitter transmits the first instruction and, when the parameter identification information is not determined by the identification information determining means, the instruction generating means generates the second instruction and the transmitter transmits the second instruction.

A second aspect of the present invention is a computer connected to a smear preparing apparatus for preparing a smear of a sample on a slide glass based on a smear control parameter, the computer comprising: a receiver for receiving sample attribute information regarding an attribute of a sample; a setting means for setting parameter identification information for identifying the smear control parameter and a condition used for determining the parameter identification information so as to be associated with each other; an identification information determining means for determining the parameter identification information on the basis of the sample attribute information received by the receiver and the condition set by the setting means; and a transmitter for transmitting the parameter identification information determined by the identification information determining means to the smear preparing apparatus.

A third aspect of the present invention is a computer connected to a smear preparing apparatus for preparing a smear of a sample on a slide glass based on smear control parameter and an analyzer for analyzing a sample and outputting analysis results of a plurality of measurement items, the computer comprising: a receiver for receiving the analysis results output from the analyzer; a memory for storing a condition regarding analysis results of a plurality of measurement items; a determining means for determining parameter identification information for identifying the smear control parameter on the basis of the analysis results received by the receiver and the condition stored in the memory; and a transmitter for transmitting the parameter identification information determined by the determining means to the smear preparing apparatus.

DETAILED DESCRIPTION OF THE PREFERRED EMBODIMENTS

Hereinafter, an embodiment of a smearing preparing system is described with reference to the drawings.

Figure 1:
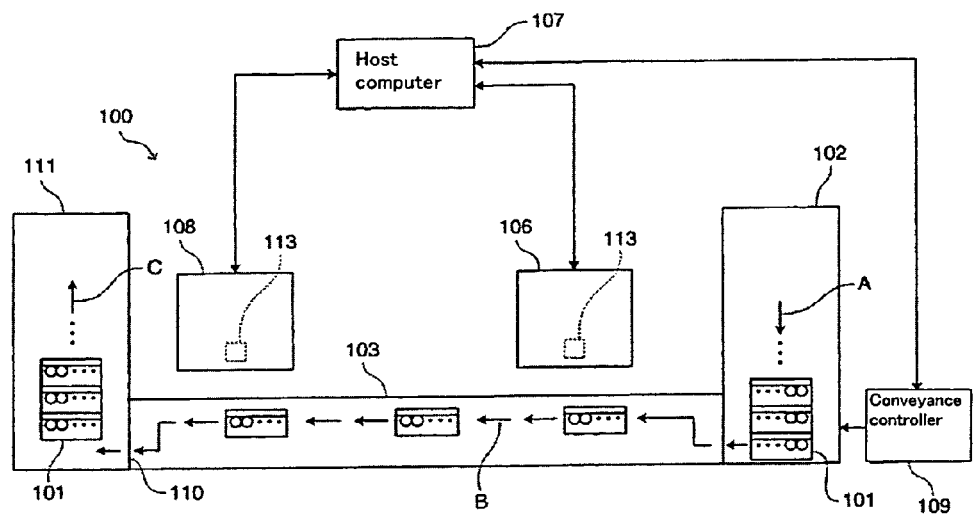
FIG. 1 is a plan view showing a smear preparing system embodying features of the present invention.

As shown in FIG. 1, a system 100 comprises a loader 102, a conveyer 103, and an unloader 111, and a blood analyzer 106, and a smear preparing apparatus 108 are arranged along the conveyer 103.

A conveyance controller 109 for controlling the loader 102, the conveyer 103 and the unloader 111 is provided and a host computer 107 which exchanges information or instructs among the blood analyzer 106, the smear preparing apparatus 108 and the conveyance controller 109 or gives instructions to them is provided.

Figure 2:
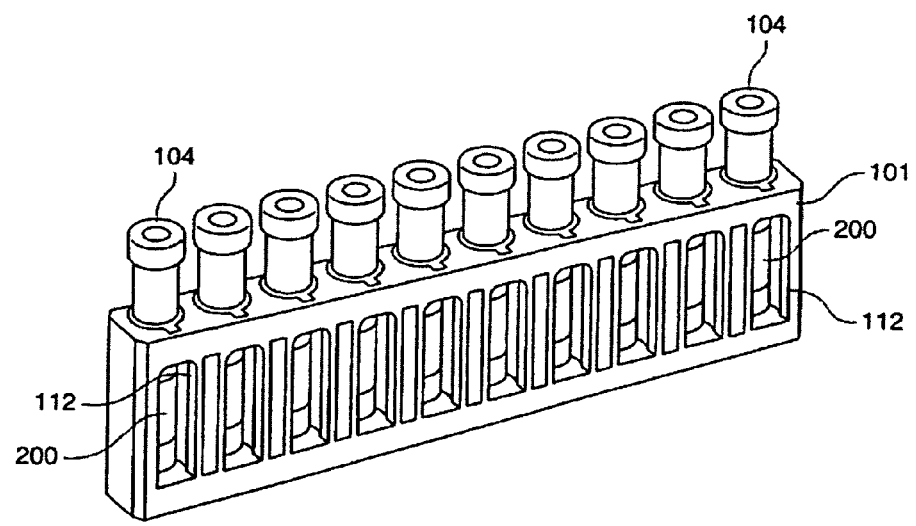
FIG. 2 is a perspective view showing sample rack embodying features of the present invention.

A plurality of sample racks 101 is put on the loader 102. The sample racks 101 are conveyed to a carry-in end of the conveyer 103 adjacent to the loader 102 in the direction shown by an arrow A and then get off the loader 102. As shown in FIG. 2, each sample rack 101 has a plurality of sample containers 104 which contain blood samples.

The sample racks 101 are conveyed by the conveyer 103 in the direction of an arrow B and reach a discharge end 110 of the conveyer 103 through in front of the blood analyzer 106 and the smear preparing apparatus 108. Then, the sample racks 101 are conveyed in the direction of an arrow C by the unloader 111 adjacent to the discharge end 110 of the conveyer 103.

In addition, as shown in FIG. 2, a barcode label 200 including identification information showing sample number (Sample ID) of the sample is attached on each sample container 104. Windows 112 are provided on the longitudinal side of the sample rack 101 through which the barcode on the sample container 104 is read.

When the sample rack 101 containing the sample containers 104 is put on the loader 102, the system 100 is started. Then, the first sample rack 101 is moved in the direction of the arrow B by the conveyer 103 and stops at the blood analyzer 106.

Here, the barcode of the first sample container 104 is read by a barcode reader 113. The blood analyzer 106 analyzes the sample in the sample container 104 and reports the analyzed result to the host computer 107 together with the barcode information. The blood analyzer 106 repeats the above operations until samples of all sample containers 104 are analyzed. The host computer 107 determines whether it is necessary to prepare the smear for that sample or not based on the analyzed result.

Then, the sample rack 101 having only the samples whose smear no longer needs to be prepared passes through the smear preparing apparatus 108 on the conveyer 103 which is controlled by the conveyance controller 109 based on a command of the host computer and reaches the unloader 111. The sample rack 101 containing the sample whose smear needs to be prepared is moved to reach the smear preparing apparatus 108 by the conveyer 103 which is controlled by the conveyance controller 109 based on the command of the host computer 107. The barcode of each sample container 104 is read by the barcode reader 113 of the smear preparing apparatus 108 and transmitted to the host computer 107. When the host computer 107 determines that the smear needs to be prepared, the smear preparing apparatus 108 takes a sample whose smear needs to be prepared from the sample container 104 and prepares a smear of blood for it. Meanwhile, the sample container 104 whose smear no longer needs to be prepared is moved further in the direction of the arrow B and the next sample container 104 reaches the smear preparing apparatus 108.

Then, the sample rack 101 which passed through the smear preparing apparatus 108 on the conveyer 103 reaches the unloader 111.

Figures 3, 4:
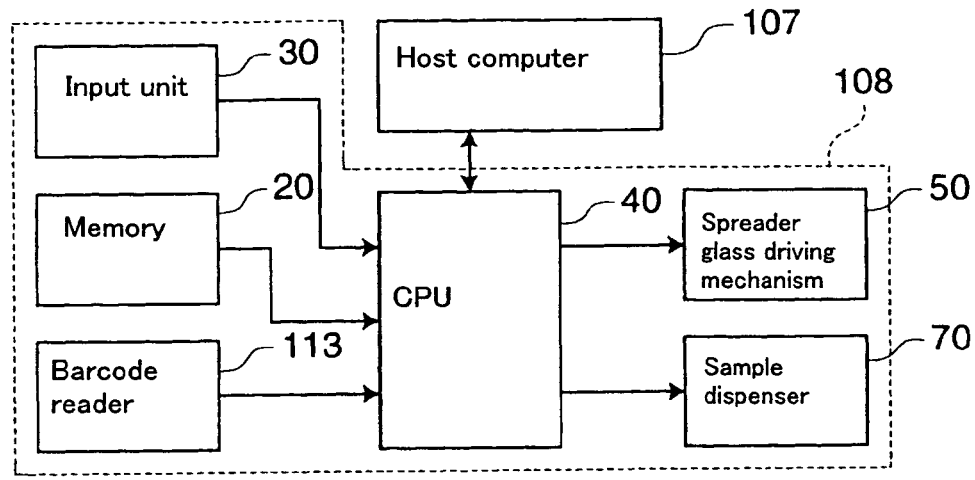
FIG. 3 is a block diagram showing the smear preparing apparatus embodying features of the present invention.
FIG. 4 is a view showing a relation between smearing levels and smear control parameters embodying features of the present invention.

FIG. 3 is a block diagram of the smear preparing apparatus 108. The smear preparing apparatus 108 comprises a memory 20, an input unit 30, a CPU 40, a sample dispenser 70, a spreader glass driving mechanism 50 and the barcode reader 113.

The memory 20 comprises a ROM, a RAM, and a hard disk. The input unit 30 comprises a keyboard.

Smear control parameters are set so as to correspond to smearing levels through the input unit 30 and stored in the memory 20. The smear control parameters are previously stored before the smearing is actually performed.

FIG. 4 is a table showing relations between the smearing levels and smear control parameters stored in the memory 20.

As shown in FIG. 4, each of the smearing levels 1 to 10 corresponds to the smear control parameters such as a speed (movement speed of a spreader glass), an angle (which is formed between the spreader glass and a slide glass), a fitting time (after the spreader glass comes in contact with sample dispensed on the slide glass until the spreader glass starts to move) and amount of dispensed sample (amount of sample dispensed on the slide glass). In addition, the smear control parameter may comprise smearing starting position on the slide glass and the like. Alternately, conditions such as speed and angle can be eliminated from the smear control parameters.

As shown in FIG. 4, default values of smear control parameters are preliminarily set with respect to all of smearing levels 1 to 10. An HCT (hematocrit value) range is made correspond to each of the smearing levels and the smearing control parameters with respect to all of the smearing levels 1 to 5. Default values are also preliminarily set for the HCT ranges. The HCT range is used, as will be described later, when the host computer 107 does not instruct a smearing level to the smear preparing apparatus 108. The smear preparing apparatus 108 is constructed so that the user can arbitrarily set the smear control parameters at the smearing levels 1 to 10 and the HCT range at the smearing levels 1 to 5.

When a replay to an inquiry for preparing a smear is received from the host computer 107, the CPU 40 reads corresponding smear control parameters from the memory 20, controls operations of the spreader glass driving mechanism 50 and the sample dispenser 70 on the basis of the read smear control parameters (speed, angle, fitting time, and amount of dispensed sample) to prepare a smear of blood.

Figure 5:
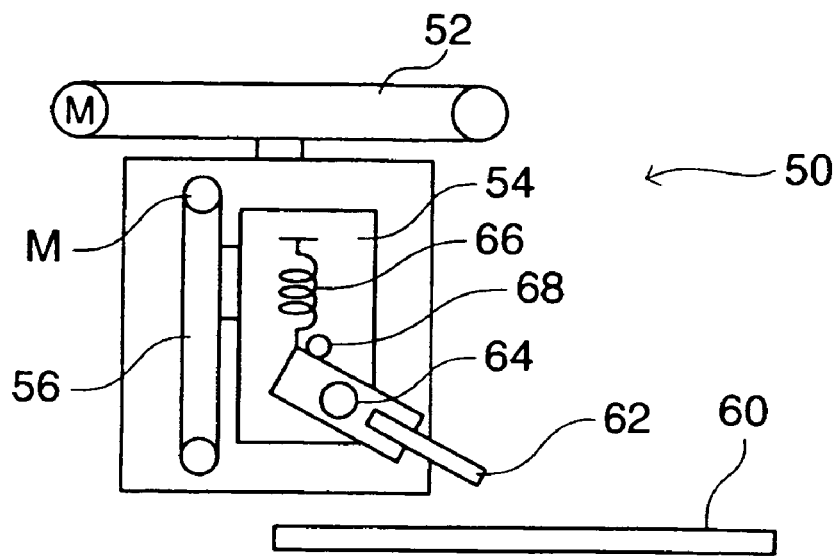
FIG. 5 is a constitution view showing a driving mechanism for a spreader glass embodying features of the present invention.

FIG. 5 is a view showing a schematic constitution of the spreader glass driving mechanism 50 in the smear preparing apparatus 108. The spreader glass driving mechanism 50 comprises a back-and-forth driving mechanism 52 which moves the spreader glass 62 parallel to the surface of a slide glass 60, a vertical driving mechanism 56 which elevates the spreader glass to and from the slide glass 60, and an angle retaining mechanism 54 which retains the angle formed between the spreader glass 62 and the slide glass 60. The back-and-forth driving mechanism 52 and the vertical driving mechanism 56 are provided for moving the spreader glass 62 back and forth, and up and down, and each comprises a belt-motor mechanism provided with a motor M and a belt.

According to the back-and-forth driving mechanism 52, a moving speed of the spreader glass 62 can be adjusted by a rotation speed of the belt motor.

In addition, the angle retaining mechanism 54 comprises an elastic member 66 which pulls the spreader glass 62 so as to be rotated around a spindle 64, and a stopper 68 which fixes a limit of rotation, in which after an end of the spreader glass comes in contact with the slide glass 60, it is further lowered so that the angle formed with the slide glass 60 is changed.

Figure 6:
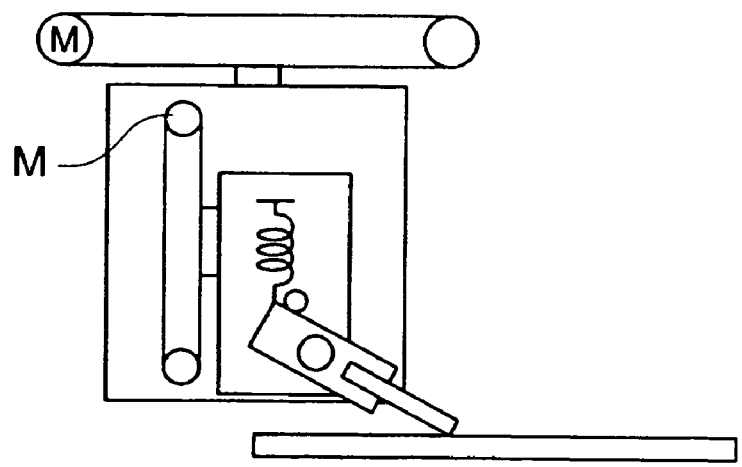
FIGS. 6 and 7 are explanatory views for operations of the driving mechanism for the spreader glass in FIG. 5.
Figure 7:
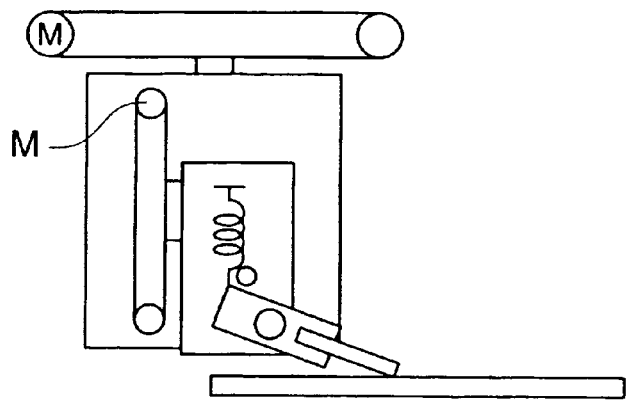

FIG. 6 is a view showing a state in which the angle between the spreader glass 62 and the slide glass 60 is retained large by the angle retaining mechanism 54 and FIG. 7 is a view showing a state in which the angle is retained small. The angle formed between the spreader glass 62 and the slide glass 60 is adjusted by an expansion state of the elastic member 66.

Figure 8:
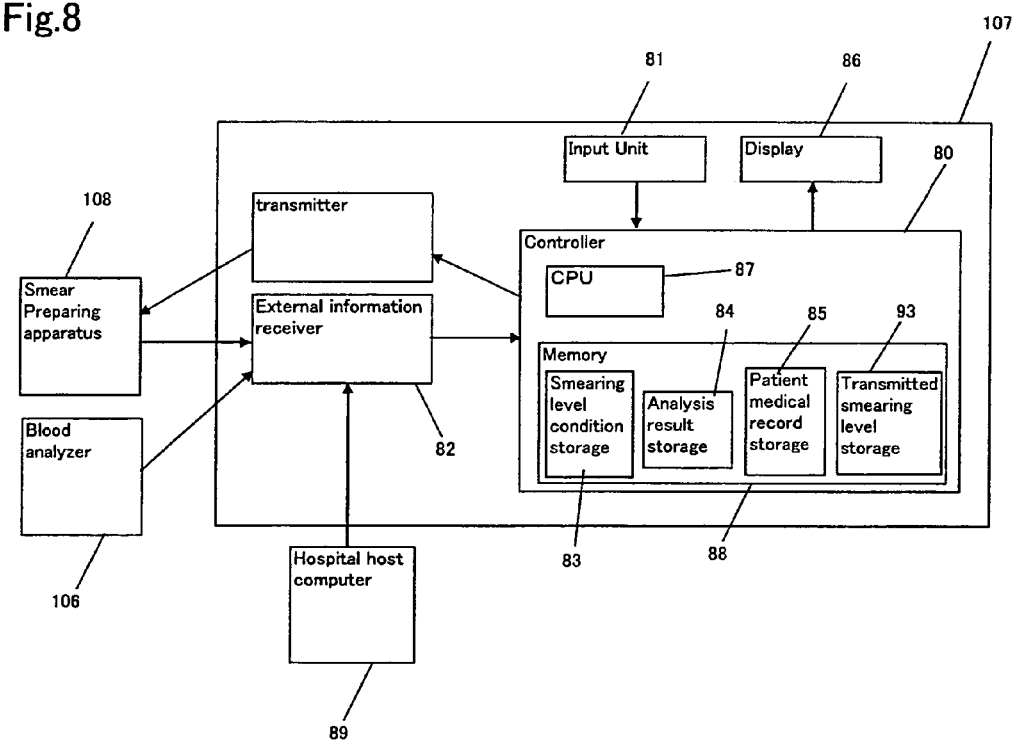
FIG. 8 is a block diagram showing a host computer embodying features of the present invention.

FIG. 8 is a block diagram showing a host computer 107. The host computer 107 has a controller 80, an input unit 81, an external information receiver 82, a display 86 and a transmitter 94. The controller 80 has a CPU 87 and a memory 88. The memory 88 has a smearing level condition storage 83, an analysis result storage 84, a patient medical record storage 85, and a transmitted smearing level storage 93. The external information receiver 82 and the transmitter 94 take the form of input/output interfaces.

The host computer 107 stores a smearing level input from the input unit 81 and smearing level conditions which are set so as to be associated with the smearing level into the smearing level condition storage 83. The host computer 107 also stores an analysis result (including a measurement value of each of measurement items and an abnormality message) from the blood analyzer 106 received by the external information receiver 82 together with a sample number (sample ID) to identify the sample into the analysis result storage 84. The host computer 107 also transmits information such as necessity to prepare a smear, a smearing level, and the like to the smear preparing apparatus 108 by the transmitter 94.

The host computer 107 also stores a medical record of a sample provider (patient) and identification information (patient ID) for specifying the sample provider (patient), received by the external information receiver 82 from a hospital host computer 89 (external terminal) into the patient medical record storage 85. The identification information for specifying the sample provider is associated with the sample number. From the sample number, the sample provider and the medical record of the provider can be specified. The display 86 displays a setting item and the details of a setting, which are input from the input unit 81 by the user. A hospital host computer 89 is a host computer for controlling the hospital in a centralized manner, and is connected to the host computer 107.

The input unit 81 comprises a keyboard and a mouse, the display 86 comprises an LCD, the external information receiver 82 and transmitter 94 comprise an I/O port, and memory 88 comprises a ROM, RAM, and a hard disk.

Figure 9:
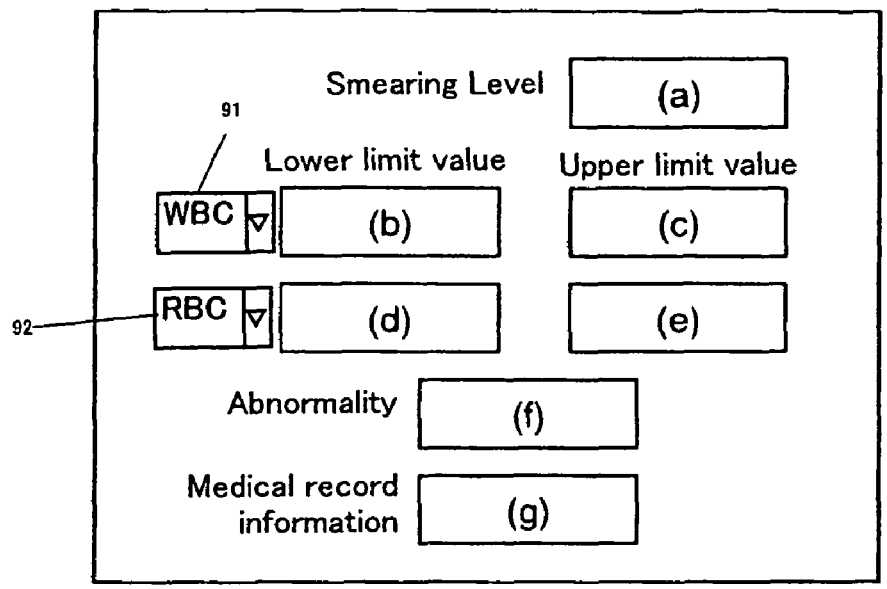
FIGS. 9 and 10 are view of screens showing conditions related to smearing level embodying features of the present invention.

FIG. 9 shows an example of a screen displayed on the display 86 when the user sets conditions (smearing level conditions) related to the smearing level by using the input unit 81.

In FIG. 9, any of 6 to 10 is input as a number indicative of the smearing level (FIG. 4) in box (a). As the smearing level conditions corresponding to the smearing level input in the box (a), the upper and lower limit values of a WBC (White Blood Cell count) are input in boxes (b) and (c), respectively. The upper and lower limit values of an RBC (Red Blood Cell count) are input in boxes (d) and (e), respectively. An abnormality message is input in box (f), and patient medical record information is input in box (g). Furthermore, the WBC and RBC can be changed to other measurement items by operating combo boxes 91 and 92 by the user.

By setting the smearing level conditions in accordance with the measurement value of a predetermined measurement item such as the RBC, WBC, or the like, a smear of blood can be prepared with special smear control parameters according to the measurement value of the predetermined measurement item. Thus, an easy-to-observe smear of blood can be prepared. By setting the smearing level conditions in accordance with measurement values of a plurality of measurement items, as compared with the case of using the measurement value of one measurement item for the smearing level conditions, various smearing level conditions can be set. This facilitates preparation of a smear of blood with a predetermined smear control parameter only from a sample matching the special condition.

An abnormality message is a message indicative of an abnormality of the sample, such as "white blood cell abnormality", "neutropenia", "neutrophilia", "lymphopenia", "lymphocytosis", "red blood cell abnormality", "anemia", "hemagglutination", "hemoglobin abnormality", "platelet abnormality" reported from the blood analyzer 106 to the host computer 107 together with numerical values (measurement values) of analysis items. One or a plurality of the messages is/are selected and set in the box (f). The abnormal messages are output from the blood analyzer 106 in the case where an analysis result of a sample matches the conditions preliminarily determined by the blood analyzer 106, and are messages indicating that occurrence of something abnormal in the sample is expected.

By using the smearing level conditions for an abnormal message, a smear of blood can be prepared with the special smear control parameters from a sample expected to have some abnormality. Thus, an easy-to-observe smear of blood can be prepared.

The patient medical record information is information described in a patient chart, such as personal information of a sample provider (age, sex, medical history, ward name, medical department, and the like), information of clinical records (information such as the name of a disease, patient's condition, and medicine being taken), and the like. In box (g), one or a plurality of pieces of the information is/are selected and set.

By using the patient medical record information as one of the smearing level conditions, the smearing level conditions can be set respectively by ward name or by disease. Consequently, a smear of blood according to the characteristics of the sample can be prepared, and an easy-to-observe smear of blood can be prepared.

The smearing level conditions may include, in addition to the above conditions, information indicating that a sample provider is in postoperative state, information indicating that the sample provider underwent or is going to undergo dialysis, a comment on to the inspection of last time (for example, a comment indicating that the quality of the smear of blood of last time was not good), or the like. The smearing level conditions do not always have to include all of the above information.

Figure 10:
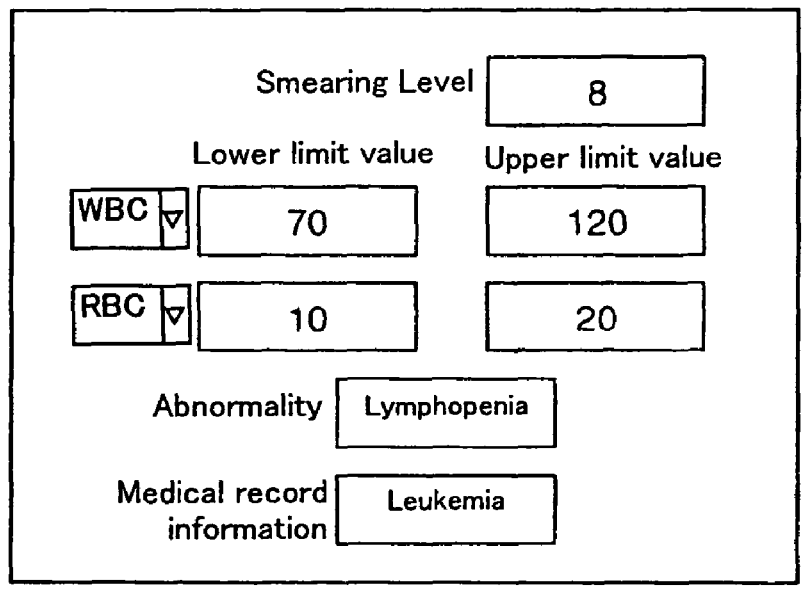

FIG. 10 shows an example of a screen displayed after the setting of the smearing level conditions is finished. The smearing level and the smearing level conditions, which are set, are stored into the smearing level condition storage 83. In the case where there are smearing levels and smearing level conditions which are preliminarily stored in the smearing level condition storage 83, the pre-stored information is replaced with the smearing level and the smearing level conditions which are input by using the screen of FIG. 9 (FIG. 10).

In the case of the smearing level conditions which are set in the screen shown in FIG. 10, the blood analyzer 106 outputs the information that the WBC is larger than 70 and smaller than 120, the RBC is larger than 10 and smaller than 20, and "lymphopenia" as an abnormality message. In the case where the patient medical record information of the sample provider includes "leukemia", the smearing level is determined as "8". A box in which a condition is not set is made blank. For example, if the boxes of the abnormality message and the patient medical record information are made blank, in the case where the WBC is larger than 70 and smaller than 120 and the RBC is larger than 10 and smaller than 20, the smearing level is determined as "8" regardless of the presence or absence of the abnormality message and the patient medical record information.

When the host computer 107 is delivered to a facility such as a hospital, default values of the smearing level and the smearing level condition are preferably pre-stored in the smearing level condition storage 83. Consequently, the user can prepare a smear of blood by a predetermined smear control parameter without newly setting the smearing level conditions.

Figures 13, 14:
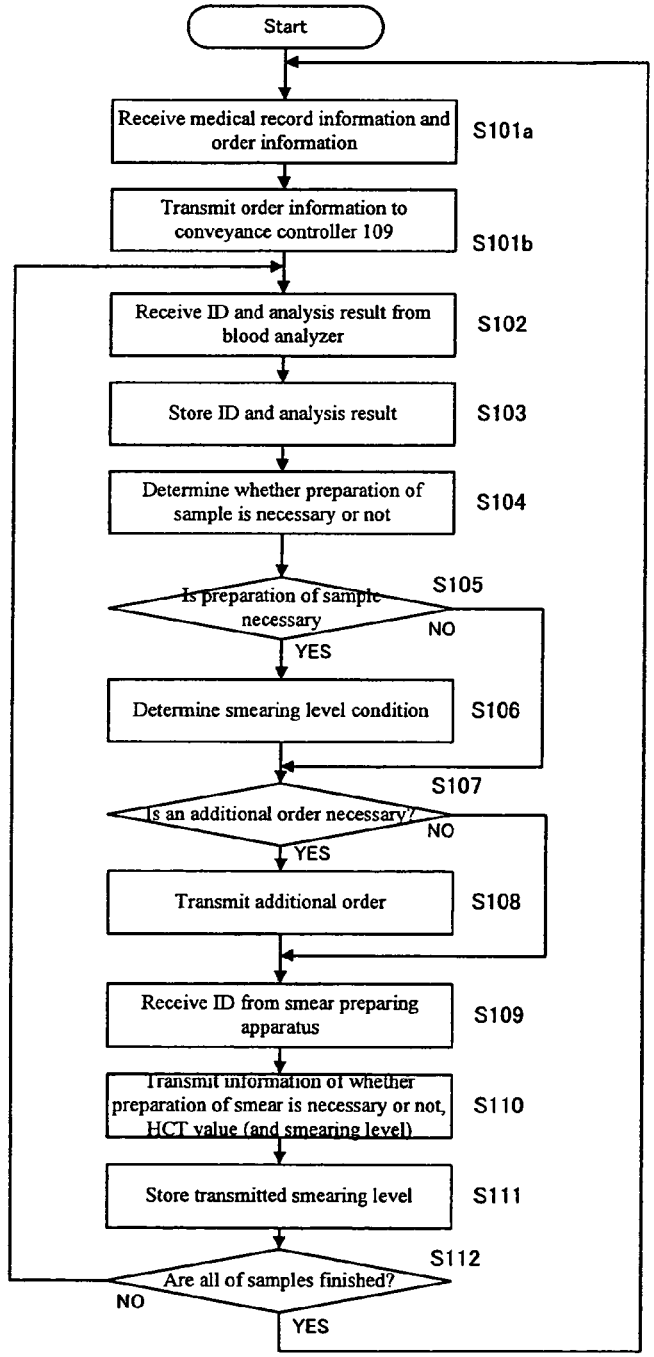
FIG. 13 is an explanatory view showing a setting example of the smearing level and conditions related to the smearing level embodying features of the present invention.
FIG. 14 is a flowchart showing processes executed by a controller 80 of a host computer 107 according embodying features of the present invention.

FIG. 13 shows an example of a table created as a result of setting of a smearing level and a smearing level condition by the user in FIG. 9. The table is stored in the smearing level condition storage 83. In the table, for example, a sample having a WBC measurement value which is larger than 40 and smaller than 70, having an RBC measurement value which is larger than 300 and smaller than 500, and having no abnormality message, and to which no patient medical record information is input satisfies the smearing level conditions corresponding to the smearing level 6. In this embodiment, when a sample satisfies all of conditions such as the WBC measurement value and the RBC measurement value, it is determined that the sample satisfies the smearing level conditions. It is also possible to determine that a sample satisfying at least one of the conditions such as the WBC measurement value and the RBC measurement value corresponds to the smearing level conditions. For instance, in the example of FIG. 13, the sample whose WBC measurement value is larger than 40 and smaller than 70, whose RBC measurement value is larger than 300 and smaller than 500, having no abnormality message, or to which no medical record information is input, may be determined as a sample corresponding to smearing level conditions corresponding to the smearing level 6.

When the sample number (sample ID) is received from the smear preparing apparatus 108, the host computer 107 extracts the analysis result and the medical record information corresponding to the sample ID from the storages 84 and 85, and determines whether a corresponding smearing level condition exists in the table shown in FIG. 13 or not on the basis of the extracted information. If there is a smearing level condition to which the extracted information corresponds, the host computer 107 transmits the smearing level corresponding to the smearing level condition and the HCT value included in the analysis result corresponding to the sample ID to the smear preparing apparatus 108. In the case where there is no smearing level condition to which the extracted information corresponds, the host computer 107 does not transmit the smearing level, but transmits the HCT value included in the analysis result corresponding to the sample ID to the smear preparing apparatus 108. The smear preparing apparatus 108, which receives the smearing level determines a smear control parameter on the basis of the received smearing level or the HCT value. As described above, the smearing level is information for identifying the smearing level condition and the smear control parameter. The smearing level condition is a condition used to determine the smear control parameter.

A series of operations of the smear preparing system 100 is described with reference to flowcharts in FIGS. 11 and 12.

Figure 11:
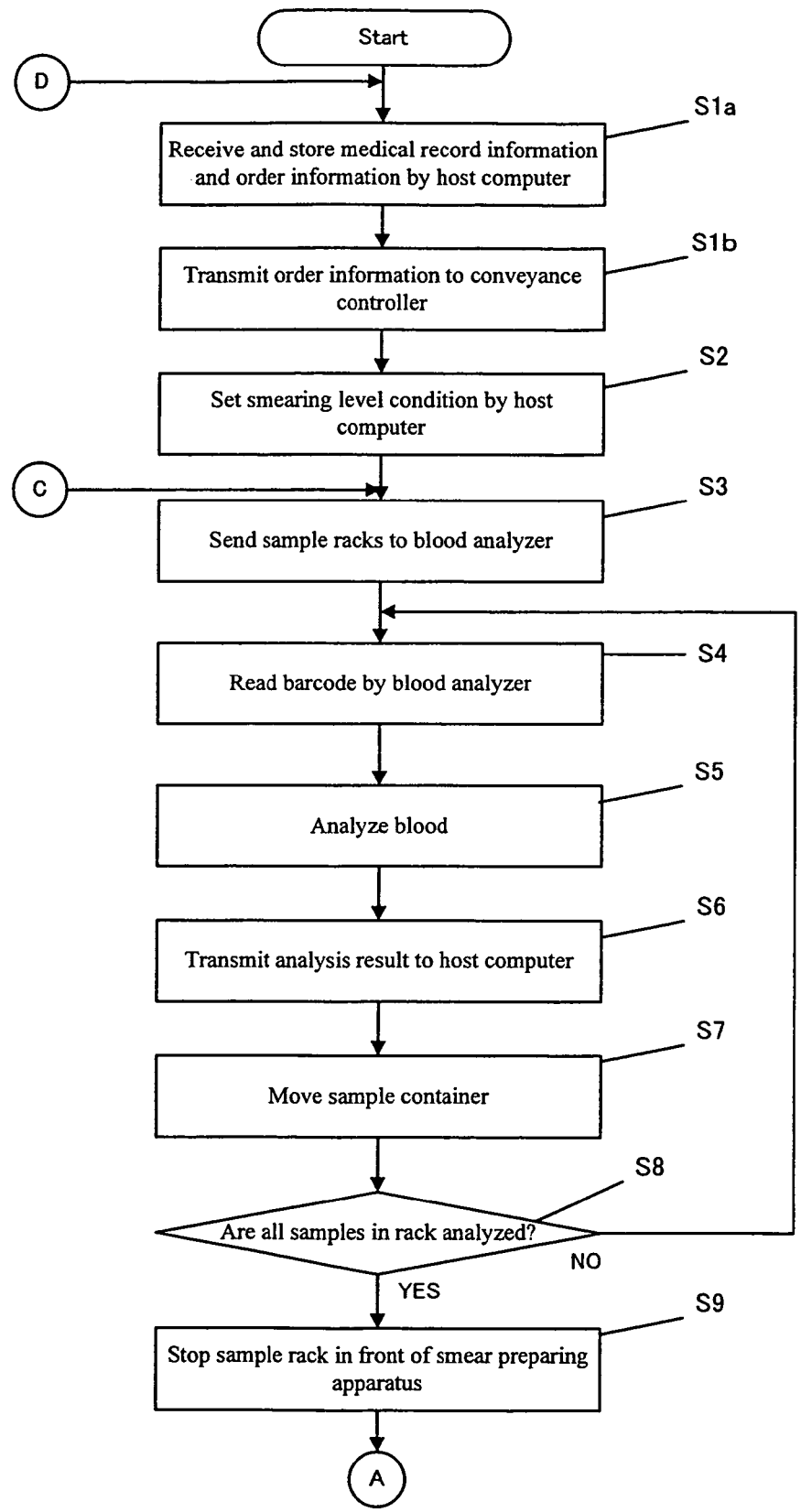
FIGS. 11 and 12 are flowcharts showing operations of a smear preparing system embodying features of the present invention.

First, in FIG. 11, the host computer 107 receives medical record information of the provider of the sample (patient) and order information from the hospital host computer 89 and stores it (step S1a). The order information is information in which the sample number (the sample ID) for identifying the sample, information of whether analysis in the blood analyzer 106 is necessary or not (presence or absence of a measurement instruction), and information of whether preparation of a smear of blood in the smear preparing apparatus 108 is necessary or not are associated with each other.

The host computer 107 transmits the order information to the conveyance controller 109 (step S1b).

Next, in the host computer 107, the smearing level and the smearing level condition are set by using the screens shown in FIGS. 9 and 10 (step S2). It is not necessary to perform the process of the step S2 every day, but it is sufficient to execute the process when preparation of a smear of blood becomes necessary in the special smear control parameter.

When a plurality of sample containers 104 (FIG. 2) containing samples and being mounted on the sample rack 101 are loaded in the loader 102 by the user, the system 100 starts and the loader 102 and the conveyer 103 are driven by the conveyance controller 109. By this driving, the sample rack 101 is conveyed to the front of the blood analyzer 106 and is stopped (step S3). The barcode (the sample number) of each of the sample containers 104 is read by the blood analyzer 106 (step S4), and the sample is sucked from the sample container 104 and is analyzed (step S5). An analysis result (a measurement value of each of analysis items and an abnormality message) is transmitted from the blood analyzer 106 to the host computer 107 together with the sample number (step S6).

The sample container 104 in which the analysis is finished is moved only by a prescribed distance (arrangement pitch of the containers 104) (step S7). In the case where there is an unanalyzed sample container 104 in the sample rack 101 (step S8), the program returns to step S4 where the barcode of the unanalyzed sample container 104 is read by the blood analyzer 106. After all of the samples in the sample rack 101 are analyzed (step S8), the program proceeds to step S9.

In step S9, the sample rack 101 to which the analysis is finished is conveyed to the front of the smear preparing apparatus 108 and is stopped.

Figure 12:
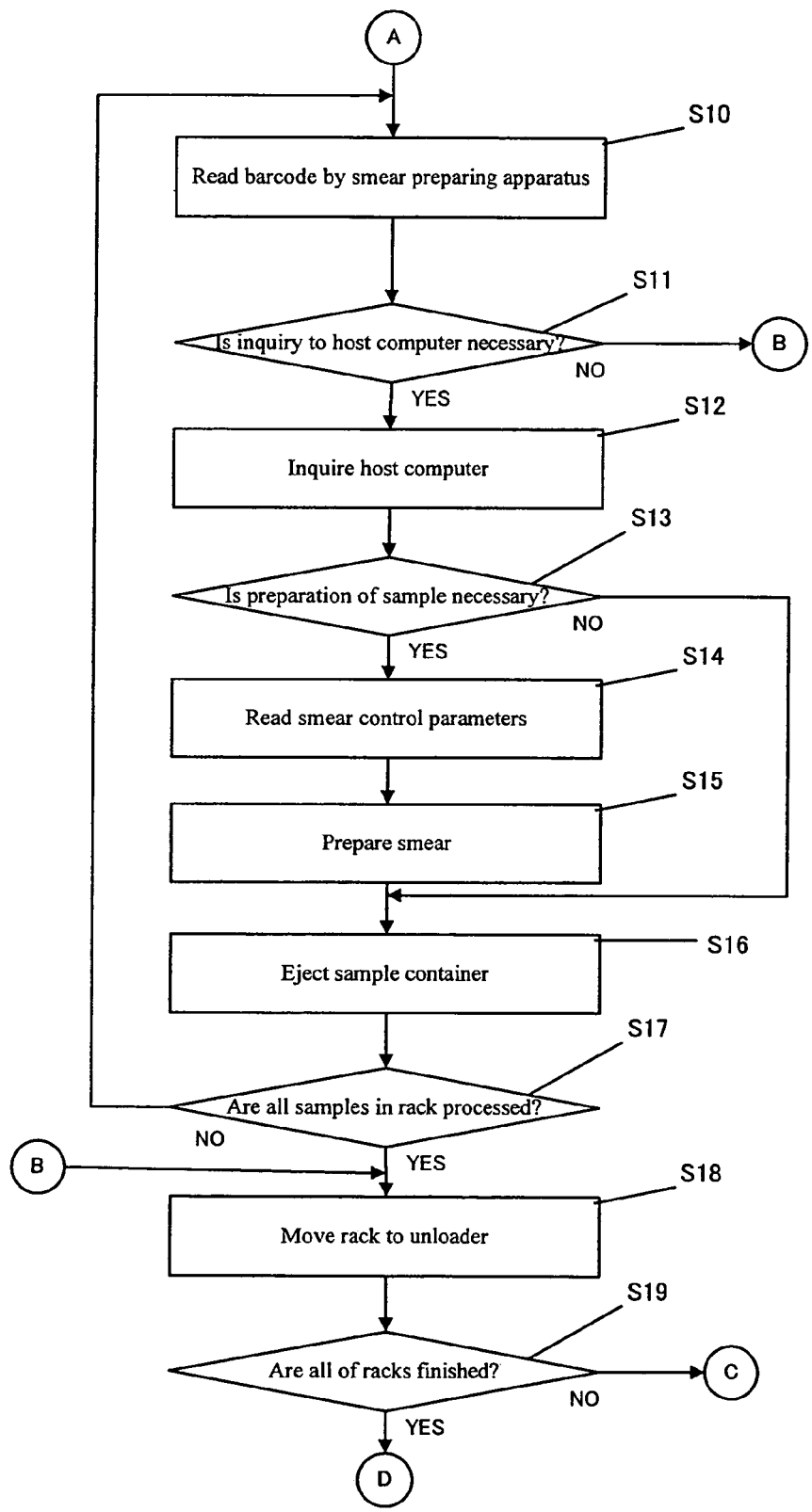

Next, as shown in FIG. 12, the barcode of the sample container 104 is read by the smear preparing apparatus 108 (step S10). The smear preparing apparatus 108 determines whether it is necessary to inquire the host computer 107 of the sample of the sample number or not. If the order information transmitted to the conveyance controller 19 in step S1b indicates that it is necessary to prepare a smear of blood, the smear preparing apparatus 108 determines that the inquiry is necessary. If the order information indicates that it is not necessary to prepare a smear of blood, the smear preparing apparatus 108 determines that the inquiry is not necessary. Even if the order information transmitted to the conveyance controller 109 indicates that preparation of a smear of blood is not necessary, in the case where an additional order which will be described later is transmitted to the conveyance controller 109, it is determined that the inquiry is necessary. When it is determined in step S11 that an inquiry to the host computer 107 is necessary, the process of step S12 is performed. When it is determined that an inquiry is unnecessary, the sample rack 110 is conveyed to the unloader 111 (step S18).

In step 12, the smear preparing apparatus 108 sends an inquiry to the host computer 107. To be more specific, the smear preparing apparatus 108 transmits the sample number read in step S10 to the host computer 107. When a reply indicating that preparation of a smear of blood is necessary is received from the host computer 107, the CPU 40 of the smear preparing apparatus 108 reads the smear control parameter corresponding to the smearing level or the HCT value received from the host computer 107 from the memory 20 (steps S13 and S14).

As shown in FIG. 4, a table in which the relations among the smearing level, the HCT value, and the smear control parameters are pre-set is stored in the memory 20. The CPU 40 reads the smear control parameters from the memory 20 on the basis of the table. Concretely, if a smearing level is transmitted from the host computer 107, the smear control parameter corresponding to the smearing level is read. If a smearing level is not transmitted from the host computer 107, the smear control parameter corresponding to the HCT value is read. In such a manner, with respect to a sample whose smear of blood has to be prepared with special smear control parameters, a smear of blood is prepared with smear control parameters set by the user. With respect to a sample whose smear of blood does not have to be prepared with special smear control parameters, a smear of blood is prepared with the smear control parameters according to the HCT value. Therefore, easy-to-observe smears of blood can be prepared for samples having various characteristics.

With the read smear control parameters, a smear of blood is prepared (step S15).

On the other hand, if it is determined in step S13 that preparation of a smear of blood is not necessary, a smear of blood is not prepared but the process of step S16 is performed. An example of cases where it is determined that preparation of a smear of blood is not necessary is a case where measurement values output from the blood analyzer 106 are in a normal range and no abnormality message is output.

In step S16, the sample container 104 in which the preparation of a smear of blood is finished is moved only by a predetermined distance (an arrangement pitch of the sample containers 104). When there is an unfinished sample container 104 in the sample rack (step S17), the program returns to step S10 and the barcode of the unfinished sample 104 is read by the smear preparing apparatus 108. After all of the samples in the sample rack 101 are processed (step S17), the program proceeds to step S18. In step S18, the sample rack 101 to which the processing is finished is moved to the unloader 111.

In step S19, whether processing on all of samples included in the order information has been finished or not is determined. If the processing on all of samples has not been finished, the program returns to step S3. If the processing on all of the samples has been finished, the program returns to the process of step S1a, and the medical record information and the order information is transmitted to the host computer 107 again.

The processes executed by the controller 80 of the host computer 107 will be described by using FIG. 14.

In step S101a, the controller 80 receives the medical record information of the provider of the sample (patient) and the order information from the hospital host computer 89. This process corresponds to step S1a in FIG. 11.

In step S101b, the order information received in step S101a is transmitted to the conveyance controller 109. As described above, the order information is information in which the sample number (sample ID) for identifying the sample, the information of whether analysis in the blood analyzer 106 is necessary or not, and the information of whether preparation of a smear of blood in the smear preparing apparatus 108 is necessary or not (the presence or absence of an instruction for preparing a smear of blood) are associated. The process corresponds to S1b in FIG. 11. Based on the order information, the conveyance controller 109, which has received the order information controls the loader 102, the conveyer 103, and the unloader 111.

In step S102, the controller 80 receives the sample ID and the analysis result of the sample from the blood analyzer 106. In step S103, the sample ID and the analysis result are stored in the analysis result storage 84. The process of step S102 corresponds to step S6 in FIG. 11.

In step S104, the controller 80 determines whether the analysis result of the sample having the sample ID received in step S102 lies within a predetermined range or not and determines whether a predetermined abnormality message is output or not. In the case where the analysis result is out of the predetermined range and the case where the predetermined abnormality message is output, it is determined that preparation of a smear of blood of the sample is necessary.

Next, based on the result of step S104, the controller 80 determines whether preparation of a smear of blood of the sample of the sample ID received in step S102 is necessary or not (step S105). If preparation of a smear of blood is necessary, the smearing level is determined (step S106). A smearing level is determined by determining the smearing level conditions in the table shown in FIG. 13 to which the medical record information received in step S101a and the analysis result received in step S102 correspond. If there is a smearing level condition to which the medical record information and the analysis result correspond, the smearing level corresponding to the smearing level condition is extracted.

If there is no corresponding smearing level condition, it is determined that there is no corresponding smearing level. When there is a plurality of corresponding smearing level conditions, the smearing level whose value is the smallest is determined as a corresponding smearing level. In the case where there are a plurality of corresponding smearing level conditions, in addition to the method of determining the smearing level whose value is the smallest as the corresponding smearing level, a method of preliminarily placing priorities on the smearing levels and determining the smearing level having the highest priority as a corresponding smearing level may be also employed.

When it is determined in step S104 that preparation of a smear of blood of the sample having the sample ID received in step S102 is necessary and the order information shows that preparation of a smear of blood is unnecessary (step S107), the controller 80 transmits an instruction (addition order) to prepare a smear of blood of the sample of the sample ID to the conveyance controller 109 (step S108). The process of the step S108 is performed before the process of step S10 in FIG. 12 is executed.

In step S109, the controller 80 receives the sample ID of the sample from the smear preparing apparatus 108. The process corresponds to the process in step S12 in FIG. 12.

In step S110, the controller 80 generates an instruction to the smear preparing apparatus 108 regarding to the sample of the sample ID received in step S109 on the basis of the results in steps S104 and S106 and transmits the instruction by the transmitter 94. The instruction includes the information of whether preparation of a smear of blood is necessary or not, the HCT value corresponding to the sample ID from the analysis result stored in the analysis result storage 84, and the extracted smearing level. When it is determined that there is no corresponding smearing level, the instruction does not include the smearing level, but includes the information of whether preparation of a smear of blood is necessary or not, and the HCT value corresponding to the sample ID. The processes of steps S109 and S110 correspond to the processes of step S12 in FIG. 12. When the instruction includes the smearing level, the HCT value may not be included.

In step S111, the sample ID transmitted in step S110, the information of whether preparation of a smear of blood is necessary or not, the smearing level, and the HCT value are stored in the transmitted smearing level storage 93. By storing the transmitted smearing level, in the case where the smear of blood is hard to observe, the smearing level can be reviewed. Consequently, the quality of the smear of blood can be further improved.

In step S112, the controller 80 determines whether the process on all of the samples included in the order information received in step S101a has been finished or not. If the process on all of the samples has not been finished, the program returns to the process in step 102. If the process on all of the samples has been finished, the program returns to the process of the step S101a, and medical record information and order information is received again.

In the flowchart shown in FIG. 14, the processes from step S102 through step S112 indicate the process on one sample. In the case that a plurality of the sample containers 104 are transmitted by the conveyer 103, the processes from step S102 through step S112 are performed on each of the sample containers 104. The processes on the sample containers 104 are executed in parallel.

Although the host computer 107 of the embodiment transmits the smearing level in step S110, the present invention is not limited to this embodiment but a smearing level condition may be transmitted. In this case, the smear preparing apparatus 108 stores a table in which the smearing level condition and the smear control parameters are associated with each other in the memory 20 and, when the smearing level condition is received, prepares a smear of blood with the smear control parameters corresponding to the smearing level condition.

Although the host computer 107 of the embodiment stores the smearing level condition and the smearing level so as to be associated with each other, the present invention is not limited to the embodiment. The smearing level condition and the smear control parameters may be stored so as to be associated with each other. In this case, the host computer 107 may transmit the smear control parameters corresponding to the smearing level condition to the smear preparing apparatus 108 in step S110. The smear preparing apparatus 108 prepares a smear of blood in accordance with the received smear control parameters.

Although the host computer 107 of the embodiment uses numeric values as the smearing levels, the present invention is not limited to the embodiment but character strings such as "for pediatrics" and "for leukemia patient" may be also used as the smearing level. As a result of this, the user can understand a usage of the smearing level easily.

Although the host computer 107 of the embodiment receives sample attribute information such as an analysis result and medical record information from the blood analyzer 106 via the external information receiver 82, the present invention is not limited to this embodiment. It is also possible to receive the sample attribute information via the input unit 81 and extract the smearing level of the smearing level condition corresponding to the received sample attribute information. In this case as well, in a manner similar to the above, the extracted smearing level condition may be transmitted to the smear preparing apparatus 108, or the smear control parameters corresponding to the smearing level condition may be transmitted to the smear preparing apparatus 108.

Although the smearing level is extracted on the basis of the sample attribute information such as the analysis result and the medical record information in the foregoing embodiment, the present invention is not limited to the embodiment. The sample ID and the smearing level may be received via the input unit 81, or the smearing level may be received together with the order information from the hospital host computer. When the sample ID is received from the smear preparing apparatus 108, the smearing level corresponding to the received sample ID may be transmitted to the smear preparing apparatus 108. In a manner similar to the above, the sample ID and the smearing level condition or the smear control parameters may be received via the input unit 81 or the smearing level condition or the smear control parameters may be received together with the order information from the hospital host computer 89.

The invention claimed is:

1. A computer connected to a blood analyzer configured for analyzing a blood sample and outputting an analysis result to the computer and a smear preparing apparatus configured for preparing a smear of a blood sample on a slide glass based on a smear control parameter, the computer comprising:
a communicator configured for communicating with the blood analyzer and the smear preparing apparatus;
a condition setter configured for setting a smear level value for identifying the smear control parameter and a value range of a count of a first blood cell, the smear level value corresponding to the value range and to the smear control parameter;
a memory; and
a controller programmed to carry out operations comprising:
receiving a setting of the smear level value and the value range by the condition setter;
storing the received smear level value and the received value range in correspondence with each other in the memory;
receiving, from the blood analyzer via the communicator, an analysis result comprising a count of the first blood cell and a hematocrit value of the blood sample, wherein the count of the first blood cell of the blood sample is at least one of a white or red blood cell count;
generating, when the count of the first blood cell of the blood sample is within the value range stored in the memory, a first instruction that causes the smear preparing apparatus to prepare a smear of the blood sample according to a first smear control parameter corresponding to the smear level value, the first instruction comprising the smear level value stored in the memory;

transmitting, when the first instruction has been generated, the first instruction to the smear preparing apparatus via the communicator;

generating, when the count of the first blood cell of the sample is not within the value range stored in the memory, a second instruction that causes the smear preparing apparatus to prepare a smear of the blood sample according to a second smear control parameter corresponding to the hematocrit value of the blood sample, the second instruction comprising the hematocrit value of the blood sample; and transmitting, when the second instruction has been generated, the second instruction to the smear preparing apparatus via the communicator;

wherein the computer and the smear preparing apparatus are disposed at different locations, and wherein the smear preparing apparatus is configured to:
  determine, when the first instruction is received, the first smear control parameter corresponding to the received smear level value and prepare a smear of the blood sample based on the first smear control parameter; and
  determine, when the second instruction is received, the second smear control parameter corresponding to the received hematocrit value and prepare a smear of the blood sample based on the second smear control parameter.

2. The computer of claim 1, wherein the first instruction further comprises the hematocrit value of the blood sample.

3. The computer of claim 1, further comprising a display, wherein the operations further comprise:
  displaying on the display a setting screen for receiving the setting of the smear level value and the corresponding value range.

4. The computer of claim 1, wherein the operations further comprise storing the smear level value included in the first instruction transmitted via the communicator in the memory.

5. The computer of claim 1, wherein the condition setter comprises an upper limit value setter for setting an upper limit value of the value range and a lower limit value setter for setting a lower limit value of the value range.

6. The computer of claim 1, wherein the operation further comprises determining whether or not the blood sample is necessary to be smeared based on the received analysis result of the blood sample.

7. The computer of claim 1, wherein the analysis result comprises a count of a second blood cell of the blood sample,
  the condition setter is configured for setting a second value range of the count of the second blood cell,
  the storing is carried out by storing the smear level value, the value range, and the second value range set by the condition setter in correspondence with each other in the memory, and
  the first instruction is generated when the count of the first blood cell of the blood sample is within the value range stored in the memory, and the count of the second blood cell of the blood sample is within the second value stored in the memory.

8. The computer of claim 1, wherein the analysis result comprises an abnormality message when the count of the first blood cell matches a predetermined condition,
  the condition setter is configured for setting a first abnormality message,
  the storing is carried out by storing the smear level value, the value range, and the first abnormality message set by the condition setter in correspondence with each other in the memory, and
  the first instruction is generated when the count of the first blood cell of the blood sample is within the value range stored in the memory, and analysis result comprises the abnormality message stored in the memory.

9. The computer of claim 1, wherein the memory further stores medical record information of a sample provider who provided the blood sample,
  the condition setter is configured for setting a first medical record information,
  the storing is carried out by storing the smear level value, the value range, and the medical storing record information set by the condition setter in correspondence with each other in the memory, and
  the first instruction is generated when the count of the first blood cell of the blood sample is within the value range stored in the memory, and the medical record information of a sample provider that provided the blood sample corresponds to the medical record information set by the condition setter.

10. The computer of claim 1, wherein the smearing apparatus comprises a memory storing the first smear control parameter correspondingly stored with the smear level value and the second smear control parameter correspondingly stored with the hematocrit value.

11. The computer of claim 1, wherein the memory comprises a plurality of smear level values and a smear level range and a smear control parameter corresponding to each smear level value in the plurality of smear level values.

12. The computer of claim 11, wherein when the count of the first blood cell of the blood sample is within multiple smear level ranges, the first instruction comprises the smear level value that is smallest among the smear level values corresponding to the multiple smear level ranges within which the count of the first blood cell is within.

13. The computer of claim 11, wherein the memory further comprises a priority identifier corresponding to each smear level, and when the count of the first blood cell of the blood sample is within multiple smear level ranges, the first instructions comprises the smear level value with the highest priority identifier among the smear level values corresponding to the multiple smear level ranges within which the count of the first blood cell is within.

* * * * *